(12) United States Patent
Colucci et al.

(10) Patent No.: US 8,349,770 B2
(45) Date of Patent: Jan. 8, 2013

(54) METHOD FOR THE PREPARATION OF A COMPOSITION BASED ON 4-HYDROXYPROLINE AND THE USES THEREOF IN THE AGRONOMICAL FIELD

(75) Inventors: Maria Gabriella Colucci, Pozzuoli (IT); Fabio Apone, Naples (IT); Maarten J Chrispeels, La Jolla, CA (US)

(73) Assignee: Arterra Bioscience S.R.L., Napoli (IT)

( * ) Notice: Subject to any disclaimer, the term of this patent is extended or adjusted under 35 U.S.C. 154(b) by 853 days.

(21) Appl. No.: 12/224,745

(22) PCT Filed: Mar. 6, 2007

(86) PCT No.: PCT/EP2007/002075
§ 371 (c)(1),
(2), (4) Date: Oct. 15, 2008

(87) PCT Pub. No.: WO2007/104489
PCT Pub. Date: Sep. 20, 2007

(65) Prior Publication Data
US 2009/0054241 A1 Feb. 26, 2009

(30) Foreign Application Priority Data
Mar. 10, 2006 (IT) .............................. MI2006A0434

(51) Int. Cl.
| | |
|---|---|
| A01N 43/36 | (2006.01) |
| A01N 43/00 | (2006.01) |
| A01N 43/04 | (2006.01) |
| A61K 31/70 | (2006.01) |
| A61K 31/715 | (2006.01) |
| A61K 31/40 | (2006.01) |
| A23B 7/10 | (2006.01) |
| A23K 1/00 | (2006.01) |
| C12P 7/06 | (2006.01) |
| C12N 9/18 | (2006.01) |
| C12N 9/24 | (2006.01) |

(52) U.S. Cl. ............ 504/287; 504/185; 514/23; 514/54; 514/57; 514/408; 514/423; 514/424; 426/53; 435/161; 435/197; 435/200

(58) Field of Classification Search .................. 504/287; 504/185; 514/23, 54, 57, 408, 423, 424; 426/53; 435/161, 197, 200
See application file for complete search history.

(56) References Cited

U.S. PATENT DOCUMENTS
4,427,587 A    1/1984 Kaneko et al.

FOREIGN PATENT DOCUMENTS
EP          0 472 987 A1    3/1992
WO    WO2004/095926 A    11/2004

OTHER PUBLICATIONS

H.B. Vickery, "Continuation and extension of work on vegetable proteins," (1937), Year Book—Carnegie Institution of Washington; 36: 325-331; Database CAPLUS. Abstract only.*
Sheen et al., "Characteristics of Fraction-1-protein Degradation by Chemicaland Enzymatic Treatments," (1987), J. Agric. Food Chem; 35: 948-952.*
H.B. Vickery, "Continuation and extension of work on vegetable proteins," (1937), Year Book—Carnegie Institute of Washington; 36:325-331; Database CAPLUS. Abstract only—previously supplied.*
Sheen et al., "Characteristics of Fraction-1 protein Degradation by Chemical and Enzymatic Treatments," (1987), J. Agric. Food Chem.; 35:948-952 (previously supplied).*
PCT Search Report Dated Jul. 9, 2007.
Cho Y-P et al; "Serine O Galactosyl Linkages in Glyco Peptides From Carrot Cell Walls" Phytochemistry (Oxford) vol. 15,No. 1, 1976 pp. 165-169.
Raggi V; "Hydroxyproline-Rich Glycoprotein Accumulation in Tobacco. Leaves Protected Against *Erysiphe cichoracearum* by Potato Virus Y Infection", Plant Pathology (2000) 49:179-186.
Akashi T et al: "Stabilization of Cortical Microtubles by the Cell Wall in Culktured Tobacco Cells Effects of Extensin on the Cold-Stability of Cortical Microtubles" Planta (Heidelberg) vol. 182, No. 3, 1990 pp. 363-369.
Lamport DTD et al: "Stress Upregulates Periplasmic Arabinogalactan-Proteins" Plant Biosystems Vol. 139, No. 1 Mar. 2005 pp. 60-64.
Azizian et al: "A Novel One-Pot Synthesis of Some New Interesting Pyrrole Derivatives" J.Org. Chem. vol. 70, No. 42005, pp. 1471-1473, (2005).
Showalter AM et al: "Accumulation of Hydroxyproline-Rich Glycoprotein Messenger RNA Species in Respose to Fungal Elicitor and Infection" Proc. Nat. Acad. Sci. of USA vol. 82, No. 19, 1985 pp. 6551-6555.
V. Avery-Fullard et al., Proc. Natl. Acad. Sci, USA, vol. 85, pp. 1082-1085, Feb. 1988.
Tetsuo Takeichi et al., Plant Physiol. (1998) pp. 477-483.
Derek T.A. Lamport, Biochemistry, vol. 8, No. 3. pp. 1155-1163, Mar. 1969.
Jong Chan Hong et al., The Plant Cell, vol. 1 pp. 937-943, Sep. 1989.
James B. Cooper et al., Biochemical and Biophysical Communications, vol. 112, No. 1, pp. 161-167, Apr. 15, 1983.
Michael Brownleader et al., Planta (1993) 191:457-469.
Yong-Pill Cho et al., Phytochemistry, 1976, voil. 15, pp. 165-169.
Xiaoyang Qi et al., Plant Physiol. (1995) 108: 1691-1701.
Miriam M Brysk et al. Biochimica et Biophysica Acta, 257 (1972) 421-432.

\* cited by examiner

*Primary Examiner* — Richard Schnizer
*Assistant Examiner* — Jane C Oswecki
(74) *Attorney, Agent, or Firm* — Hedman & Costigan, P.C.; James V. Costigan

(57) ABSTRACT

The present invention relates to a method for the preparation of 4-hyroxy-L-proline or compositions with a high content of this aminoacid and the use thereof as agrochemical in the agronomical field and/or as a synthesis intermediate of chemical compounds.

8 Claims, No Drawings

METHOD FOR THE PREPARATION OF A COMPOSITION BASED ON 4-HYDROXYPROLINE AND THE USES THEREOF IN THE AGRONOMICAL FIELD

FIELD

This application is a 371 filing of PCT/EP2007/002075 filed Mar. 6, 2007, which claims priority to Italian Patent No. MI2006A 000434 filed Mar. 10, 2006

The present invention relates to a method for the preparation of a composition based on 4-hydroxyproline and the uses thereof in the agronomical field.

In particular, the present invention relates to a method for the preparation of 4-hydroxy-L-proline and compositions with a high content of this aminoacid and the use thereof as agrochemical in the agronomical field and as a synthesis intermediate of chemical compounds.

4-hydroxy-proline, a hydroxylate derivative (4-HO-Pro) of proline, is an aminoacid of considerable biological importance which is typically found in collagen.

Hydroxyproline is currently obtained starting from protein sources of an animal, such as swine or bovine, origin.

The methods for obtaining oligopeptides rich in hydroxyproline envisage that the protein source of animal origin be initially ground and preserved in low-temperature environments until the moment of treatment, which comprises the following phases:

Acid hydrolysis (the acidity is kept high during the whole operation, to accelerate the process and pre-vent any type of racemization). The temperature varies from 70-100° C.;

Filtration of the insoluble products/decanting or extraction with solvents of the lipidic or lipophilic components;

Purification by ion-exchange chromatography. The hydroxyproline content in the richest matrixes can reach, at the maximum, 12-14% of the aminoacid mass, with the presence of similar quantities of aminoacids, for example proline (10-15%), which make the operating parameters for the separation critical;

Purification/decolouration with activated carbons;

Ultrafiltration;

Repeated crystallization;

Drying.

However, the processes currently used have various disadvantages such as obtaining a total concentration of free or peptide hydroxyproline lower than 12-14% with respect to the aminoacidic mass present, in addition to the risk of contamination by dangerous bioactive peptides. This can be associated with risks of contamination by a modified protein (with respect to the "non-pathological" form) called "prion" responsible of the development of some serious pathologies among which bovine spongiform encephalopathy (BSE).

These risks have recently led the European Union to forbid the use of hydrolyzed proteins of animal origin or derivation for use in biological agriculture.

Three groups of glycoproteins rich in hydroxyproline (Hydroxy-Rich-Glyco-Protein, HRGP), identified and characterized in plants, are described in literature (Showalter A M and Varner J E (1988); Biochemistry of Plants, Vol. 15, edited by Stumpf P K & Conn, EE Academic Publisher, New York). These include:

i) "arabinogalactan proteins", mainly localized in the extracellular matrix and sometimes associated with the plasmatic membrane;

ii) lectins belonging to the Solanaceous family; and iii) extensins, the main components of the primary cellular wall where they covalently bind the hemicellulose matrix and pectins. They are particularly abundant in the walls of cells grown in liquid mediums (Lamport, 1974; Cooper and Varner, 1983; Qi et al., 1995).

Some of these extensins coming from carrot cell cultures were widely characterized for their important role in the control of the wall extension during cellular growth (Lamport, 1969; Brysk and Chrispeels, 1972). More recently, new proteins similar to extensins, containing 20% of proline and 20% of hydroxyl-proline, were extracted from cell walls of soya in a culture and widely characterized (Averyhart-Fullard et al., 1988; Hong and Nagao, 1989).

The solubilization of HRGP from cell walls was performed by various research groups with analogous methods. The first works go back to 1969, when a first purification and identification of the proteins linked to the cell wall were performed (Lamport, 1969). A similar protocol based on the removal of sugar chains bound to the glycoproteins of the wall with hydrochloric acid and consequent treatment with tripsin, was subsequently applied to cultures of carrot cells for the isolation and analysis of peptides rich in hydroxy-proline deriving from the hydrolysis of the glycoproteins of the wall (Cho and Chrispeels, 1976).

Protocols based on the tripsinization of glycoproteins of the wall were also successfully applied to cultures of cotton cells (Qi et al., 1995).

Proteins similar to extensins were purified from soya cell walls with processes based on strong treatment with trichloroacetic acid, which hydrolyze the glucoside bonds of these glycoproteins and also allow their detachment from the cellulose matrix, and consequently isolated by more modern HPLC techniques (Averyhart-Fullard et al., 1988). Analogous treatment with strong acids and gel filtration processes were also used for isolating and characterizing the extensins of the wall of tomato cellular cultures (Brownleader and Dey, 1993).

Only a few studies oriented towards the sole characterization of said glycoproteins and experimental verifications of their function in vegetable physiology, are currently known.

4-HO-Pro (Plant Physiology (1984), "Effects of the Proline Analog L-Thiazolidine-4-carboxylic Acid on Proline Metabolism", Vol. 74, pages 213-218, 1984) is also known for being capable of increasing the proline level in vegetable tissues, reinforcing the natural responses of the plant to mitigate/oppose the effects caused by abiotic stress agents (for example, extreme temperatures, drought, salinity of the soil, but also various kinds of chemical contaminations), and also to assist the responses of the plant or the effect of exogenous phytoiatric agents in the control of phytopathogens.

4-HO-Pro coming from animal sources is in fact already commercialized for this purpose, but only in a mixture with other aminoacids. For these applications, it is in fact only available diluted in protein hydrolyzed products and, in particular, hydrolyzed products coming from chemical or enzymatic treatment of animal epithelium. This source however represents a possible risk of contamination due to the potential presence of bovine spongiform encephalopathy (BSA) vectors.

In the present state, the availability of alternative sources for obtaining 4-HO-Pro reducing the risks of biological contamination has become necessary.

One of the objectives of the present invention therefore consists in providing a method for obtaining 4-hydroxy-L-proline or compositions enriched in this aminoacid in free form or in the form of oligopeptides, which is without risks of biological contamination.

A further objective of the present invention consists in providing 4-hydroxy-L-proline or compositions based on this aminoacid which can be used as intermediates for the preparation of other chemical substances.

Another objective of the present invention consists in providing compositions based on hydroxyproline which can be applied in the agronomical field and in particular in biological agriculture.

In view of the above objectives, in accordance with a first aspect of the present invention, a method is provided for the preparation of a composition comprising 4-hydroxyproline according to claim 1.

Further accessory characteristics of the method of the invention are indicated in the enclosed dependent claims 2-7.

The Applicant has found that by starting from plant cell cultures and in particular by suitably treating the cell walls of varies plant species, it is possible to obtain compositions of aminoacids rich in 4-hydroxy-L-proline, substantially free of other biological contaminants.

In particular, according to an embodiment of the invention compositions enriched in 4-hydroxy-L-proline are obtained through the fermentation of plant cell cultures, the separation and lysis of the cellular walls of the cells.

According to another embodiment, the method of the invention also comprises the degradation of the proteins into peptides based on poly-4-HO-Pro released by the lysis of the cellular walls chemically and/or enzymatically, and the optional purification, either partial or total, of the 4-HO-Pro thus obtained, as free aminoacid.

According to a preferred embodiment of the invention, the starting cellular culture is based on BY2 cells of tobacco.

The characteristics and advantages of an embodiment of the method according to the present invention will appear more evident from the following illustrative and non-limiting description, referring to the following scheme which comprises the following phases:

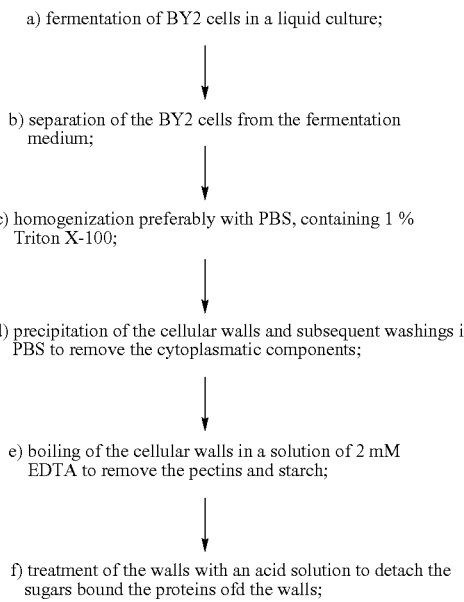

a) fermentation of BY2 cells in a liquid culture;

b) separation of the BY2 cells from the fermentation medium;

c) homogenization preferably with PBS, containing 1 % Triton X-100;

d) precipitation of the cellular walls and subsequent washings in PBS to remove the cytoplasmatic components;

e) boiling of the cellular walls in a solution of 2 mM EDTA to remove the pectins and starch;

f) treatment of the walls with an acid solution to detach the sugars bound the proteins ofd the walls;

-continued g) digestion of the proteins of the walls, in acid medium and/or enzymatically;

h) separation by chromatography of the peptides and aminoacids.

Phases a-h are conveniently effected according to the following procedures and conditions:

a) Fermentation of the vegetable cells, preferably BY2 of tobacco, in a liquid medium: the fermentation can be carried out as described for example by Kato et. al, 1972, by inoculating 50 ml of a dense cell culture in 1 L of culture medium, containing 30 g/L of saccharose, 4.4 g/L of Murashige/Skoog Basal Salt Mixture (MS salt, Sigma), 0.1 g/L of inositol, 1 mg/L of thiamine, 0.2 mg/L of 2.4 D, 0.18 g/L of $KH_2PO_4$ at pH 5.7.

The fermentation can also take place in different volumes and modified culture mediums with respect to that proposed by Kato et al.

b) Separation of the BY2 cells: this can be effected by sedimentation of the cells and subsequent filtration of the liquid through a layer of Miracloth fabric (Calbiochem), which withholds the cells but allows the passage of the aqueous solution. According to another embodiment, it can be effected by centrifugation or also by simple decanting of the culture medium. The cells are then collected with any collection system, for example a spatula, which can be convenient and resuspended in PBS (1.44 g/L of $NaH_2PO_4$, 0.24 g/L of $KH_2PO_4$, NaCl 8 g/L at pH 7.4) containing a detergent, for example Sodium Dodecyl Sulfate (SDS) at 1%. The suspension buffer can differ from PBS both with respect to the chemical composition and pH. The SDS can be substituted by other detergents which can be more suitable for the quantity of cells used.

c) Homogenization of the BY2 cells: the homogenization of the cells can be effected in a suitable container such as a ceramic mortar and with a pestle also ceramic. The quantity of cells and the relative buffer volumes to be used vary in relation to the preselected procedure. The homogenization can also be effected with presses of the mechanical or hydraulic type or by other apparatuses available on the market suitable for the breakage of the cells by friction, under cooled and non-cooled conditions.

d) Precipitation of the cellular walls: once a homogeneous cellular lysate has been obtained by means of homogenization, the sample of cells is centrifuged, for example at 3000 r per 15 minutes approximately, to precipitate the cellular walls. The supernatant obtained from the centrifugation is eliminated, whereas the pellet of the walls is washed three times with a buffer until all the cytoplasmatic components and detergent have been eliminated from the supernatant.

e) Boiling of the cellular walls: the cellular walls thus obtained are boiled in the presence of a sequestering agent, for example EDTA 2 mM, to eliminate the pectins and starches which contaminate the wall preparation. The pellet thus obtained is washed again in PBS.

f) Treatment of the walls with an acid solution: the pellet of cell walls is resuspended in an acid solution, for example HCl 0.1 N (pH 1.0) and boiled, typically for about 1 hour. In this way, all the sugars covalently bound to the wall proteins are detached and brought into solution. The wall proteins are now accessible to the attack of the proteolytic enzymes which hydrolyze them into peptides and/or single aminoacids.

g) Digestion of the wall proteins: this can be advantageously effected with acid mediums or enzymatically, or using both methods, by alternating, for example, the enzymatic hydrolysis with acid hydrolysis. For the acid treatment, inorganic acids are used, for example, hydrochloric acid, sulfuric acid, phosphoric acid, nitric acid; or organic acids such as acetic acid, trifluoroacetic acid, methanesulfonic acid, trifluoromethanesulfonic acid. When said digestion is performed enzymatically, proteolytic enzymes can be used, such as for example, tripsin (with methods typically described in Cho and Chrispeels, 1976) but preferably with pepsin, which allows the treatment to be effected directly in the acid solution used for the hydrolysis of the sugars, without the need for further washings or neutralizations with bases.

h) Separation of the aminoacids by chromatography: a further purification can be carried out on the mixture of peptides/aminoacids extracted from the walls to separate the protein components having various molecular weights from the sugars, prevalently arabinoses. This can be effected with weak ion exchange chromatography or gel filtration, using Dowex50 columns (ion exchange) or Sephadex G10 or G15 gel filtration columns (gel filtration).

According to another aspect a polypeptide-based composition is provided, comprising 4-hydroxyproline obtained according to the method of the invention.

According to another aspect, the use is provided of 4-hydroxyoproline or a polypeptide composition comprising 4-hydroxyproline, obtained according to the method of the invention in the agronomical field, in particular to give crops a greater tolerance to abiotic and/or biotic stress i.e. caused by phytopathogen microorganisms.

The Applicant has in fact surprisingly found that 4-HO-Pro and compositions containing 4-HO-Pro, object of the present invention, are capable of significantly inducing genes involved in the self-defense of plants, for example, through the induction of the defense protein induced by pathogen attacks (Pathogen Related 1, PR1).

In particular, the Applicant has observed a significant effect of 4-hydroxy-L-proline and compositions enriched in this aminoacid, object of the present invention, for controlling the development of agents responsible for biotic stress, such as phytopathogen microorganisms, through the induction of substances having an anti-fungal activity, such as the defense protein PR1.

According to an embodiment, the use is envisaged in the agronomical field, in particular in biological agricultural crops, of compositions comprising 4-HO-Pro in the presence of polysaccharides, typically arabinose chains, present in the BY2 cell walls of tobacco, optionally separated from the protein matrix, but not removed from said composition.

Furthermore, the 4-HO-Pro obtained with the method of the invention also allows different associations to be obtained for example with pre-determined aminoacids, or with polysaccharides or with osmoprotectors of a varying chemical nature and/or action mechanism, and also facilitates separation operations of 4-HO-Pro with a high degree of purity for synthetic uses (such as for the production of peptides with particular quaternary structures).

Another embodiment envisages the agronomical use of cellular walls, preferably BY2 cells of tobacco, by assimilating the degradation process described above to its natural metabolism produced on or within the plant, or in the ground, by the action of microorganisms or the plant itself, and the synergic effect that the hydroxyproline component and the arabinoside component produce to limit or mitigate the effects caused by abiotic and biotic stress.

The hydroxyproline and/or the compositions based on this aminoacid obtained according to the method of the invention can be used for the treatment of the whole plant, or a portion thereof. They can therefore be applied to the leaves, but also to the trunk or stem, or to the roots by spraying solutions or suspensions or by the incorporation of granules or powders in the ground. The seeds can also be conveniently treated with the compounds object of the present patent, as a result of the osmoprotective properties shown.

The hydroxyproline and compositions obtained according to the invention can be applied to all types of crops, monocotyledon or dicotyledon, and consequently provide excellent assistance for the cultivation, for example, of cereals, fruit trees, legumes, solanaceous crops, various types of vegetables, but also ornamental plants, oleaginous plants for non-alimentary uses, lawns, etc.

Said compositions can be used alone or in a mixture with any other product traditionally used in agronomy, in any ratio or applicative procedure, both for the protection of crops (fungicides, herbicides, insecticides nemoatocides, biostimulants), but also for their nutrition (manure, various kinds of fertilizers, microelements).

An object of the invention also relates to compositions based on 4-HO-Pro, deriving from the process described above and with differing degrees of purity, optionally containing associated saccharides.

The application doses, expressed as a ratio with the weight content of 4-HO-Pro present in a litre or kilogram of composition of the invention, can vary, for example, from 0.005 g of 4-HO-Pro/hl to 5000 g of 4-HO-Pro/hl, preferably from 0.05 g of 4-HO-Pro/hl to 500 g of 4-HO-Pro/hl, even more preferably from 0.5 g of 4-HO-Pro/hl to 100 g of 4-HO-Pro/hl. This aminoacid and compositions enriched therein have the further advantage of being free of biological contaminants and consequently of being able to be used freely in the field of biological agriculture.

According to another aspect of the invention the use is envisaged of a 4-hydroxyproline or polypeptides containing 4-hydroxyproline as intermediates for preparing synthesis molecules.

For illustrative but non-limiting purposes of the present invention, some examples are provided below, relating to the preparation of compositions enriched in 4-HP-Pro according to the invention and the biological activity thereof.

EXAMPLE 1

Isolation of Peptides Rich in Hydroxyproline from BY2 Cell Walls

The BY2 cells were obtained by means of fermentations carried out as described by Kato et al., 1972. 50 ml of a dense cell culture was used as starting material for inoculating 1 L of culture medium, containing 30 g/L of saccharose, 4.4 g/L of Murashige/Skoog Basal Salt Mixture (MS salt, Sigma), 0.1 g/L of inositol, 1 mg/L of thiamine, 0.2 mg/L of 2.4 D, 0.18 g/L of $KH_2PO_4$ at pH 5.7. The culture is then incubated at 27° C., in the dark, under constant orbital stirring (110 rpm) and after 8 days the cells are filtered through a layer of Miracloth fabric (Calbiochem), and homogenized in a mortar in the presence of SDS (Sodium Dodecyl Sulfate) 1% (or TritonX-100, 1%) in a PBS buffer (Phosphate Buffer Saline: 1.44 g/L of $NaH_2PO_4$, 0.24 g/L of $KH_2PO_4$, NaCl 8 g/L at pH 7.4). The resulting lysate is first boiled in the presence of EDTA, treated with HCl 0.1 N and then digested with pepsin in an acid environment. This procedure leads to the solubilization of the protein fraction present in the cell walls, quantifiable with the Bradford test (Bradford, 1976) or with the addition of ninhydrin.

More specifically:

BY2 cells (300 g), deriving from 1 L of culture, are homogenized in a mortar with about 300 ml of PBS containing 1% SDS (or TritonX-100). The lysate obtained is centrifuged at 3,000 rpm to precipitate the cell walls which are then washed with further quantities of PBS to remove the cytoplasmatic components.

The product obtained, defined as composition Nr. 1, can be used for agronomical applications.

The additional boiling of the cellular walls in 150 ml of EDTA 2 mM allows the removal of the pectins and starch. The walls are then treated with HCl 0.1N (150 ml) to detach the sugars bound to the wall proteins, obtaining Composition Nr. 2 which, once neutralized with NaOH and suitably diluted, can be used for agronomical applications.

Pepsin (1 mg/ml) is then added to digest the wall proteins, maintaining the pH at a value of 1.0, in a volume of 150 ml. The protein quantity obtained from the digestion is measured with the Bradford method, using BSA (Bovine Serum Albumine) as standard.

The peptides thus obtained (about 120-130 mg) in acid solution which also contains the saccharide fraction, are lyophilized and resuspended in a buffer solution (pH 6) for biological testing (Composition Nr. 3).

EXAMPLE 2

Further Purification of the Peptides Rich in Hydroxyproline from BY2 Cell Walls Separation by Chromatography of the Aminoacids Composition Nr. 3, deriving from the digestion of the walls with acid and pepsin, was lyophilized and resuspended in 10-15 ml of a pyridine-formate buffer 10 mM, pH 3.3, to be applied on a chromatographic column previously washed and balanced with a pyridine 1 mM buffer.

Columns containing Dowex 50WX2-400 resin (Sigma), used in weak ion exchange chromatography, are charged with material deriving from the acid and protein digestions of the walls. The column thus charged is eluted first with pyridine formate 1 mM, pH 3.3, and subsequently with a pyridine buffer 750 mM. The charged molecules, such as aminoacids and peptides, are withheld by the column and are not eluted with the first elution of pyridine formate. The 1 mM buffer only elutes neutral or weakly charged molecules, such as sugars. Elution with a pyridine buffer at higher concentrations also allows charged molecules, such as aminoacids and peptides, to be eluted.

In gel filtration chromatography, columns, containing Sephadex G10 resin (Sigma), allow molecules with a molecular weight lower than 700 Da to be separated. Gel filtration exploits the dimension of the molecules for the separation, larger molecules such as fragments of protein or more voluminous peptides are eluted first, unlike small molecules, such as aminoacids or simple sugars, which are withheld by the porosity of the resin, are eluted with larger buffer volumes. The same pyridine formate buffer at pH 3.3 can also be applied to Sephadex columns to elute the peptides and subsequently the single aminoacids deriving from the hydrolysis of the proteins of the cell wall.

In both cases, the advantage in using a pyridine formate buffer is its high volatility which allows it to be easily eliminated after lyophilization, in order to recover the peptide component free of contaminations by salts or other organic molecules.

EXAMPLE 3

Expression of Abiotic and Biotic Antistress Genes PDH, GSTF7, PR1 Following the Treatment of Plants with Compositions Containing Hydroxyproline Composition Nr. 3, deriving from the digestion of the walls with acid and pepsin, was lyophilized and resuspended in 15 ml of a 250 mM solution of NaOH, in order to have a final pH equal to 6.0. One ml of this solution was additionally diluted in 10 ml of distilled water, to be used directly on plants of *Arabidopsis thaliana*. *Arabidopsis* plants, Columbia ecotype, grown in soil for 3-4 weeks and exposed to light for a period of 16 hours, were sprayed on the leaf surface with composition Nr. 3. After 24 hours, some of the leaves were removed from each sample and the total RNA extracted with the Sigma kit. The cDNA was synthesized using the products Promega and Fermentas.

Quantitative PCR experiments on various genes involved in plant defence response were performed using a kit purchased from the company Ambion, in which two pairs of primers/competimers are used for the amplification of the gene of the ribosomal RNA 18S, which represents the control standard.

Analysis of gene expression was carried out on three genes, which represent excellent molecular markers for revealing and quantifying the defense response of the plant with respect to both abiotic and biotic stress. The genes analyzed are those which encode the dehydrogenase proline enzyme (PDH), described by Hua et al., 2001, that of a glutathione s-transferase (GST-F7) (Bechtold et al., 1993), and that of the protein PR1 (pathogenesis related protein 1) (Lebel et al., 1998). The first two genes are involved in the defense response of plants to stress of the abiotic type, which are generally induced by an increase in proline in the plant.

The last gene, on the other hand, is involved in the response to stress of the biotic type, i.e. it is activated following the attack of pathogen organisms and induces a response generally mediated by salicylic acid.

In various experiments it is demonstrated how treatment with composition Nr. 3 leads to a significant induction of both the PDH and GST-F7 genes (response to abiotic stress) and also the PR1 gene (response to biotic stress).

EXAMPLE 4

Synergy of the Presence of Sugars in the Expression of Genes Responsible for the Mitigation of Abiotic and Biotic Stress Induction experiments of the same genes were performed, using the material of composition Nr. 3 fractionated on a Dowex50 column. The different fractions, obtained by elutions with a pyridine formate 1 mM buffer and mainly containing sugars, were tested on plants under the same conditions described above and gave a weak inductive effect. The protein components, both larger peptide fractions and single aminoacids (prevalently represented by hydroxyproline) gave a significantly higher response in the expression of the stress marker genes. The effect on the gene expression produced by composition Nr. 3 is higher with respect to that produced by the single fractionated components, this suggests a synergic action of the glucoside component together with the protein component. The response effect of plants to stress was evaluated by also analyzing other genes, important markers of both abiotic and biotic stress. The other genes analyzed, which provided analogous results, are SAG29 (Senescence Associated Gene 29), SAG12 (Senescence Associated Gene 12), WHY1 (Whirly 1), TGA2 (transcription factor), COR47 (involved in salt stress and drought), CAT3 (encoding for a catalase), LOX2 and ERF1 (both involved in biotic stress response).

EXAMPLE 5

Mitigation of the Effects of Abiotic Stress on Bean Plants

Bean plants grown in a high salinity medium were treated with composition Nr. 3, applying a dose equal to 50 g/hl of aminoacid-protein component per plant (thesis 2). These plants were compared with plants grown in the same saline medium, but not treated (thesis 3) and with plants grown in a medium with the same composition but non-saline (thesis 1). 4 plants were used for each thesis, kept in a greenhouse for 8 days and then visually compared. Thesis 3, not treated, has an extensive necrotization of the tissues, whereas thesis 2 has a high reduction of the effects caused by the high salinity, having a development and condition similar to the plant grown in the absence of salinity and demonstrating the capacity of composition Nr. 3 of mitigating the effects caused by typical abiotic stress.

The same experiment was obtained with compositions Nr. 1 and Nr. 2, again at a dosage of 50 g/hl of aminoacid-protein component, obtaining analogous results.

The invention claimed is:

1. A method for the isolation of polypeptides containing 4-hydroxyproline and sugars, characterized in that it comprises the following steps:
   a) fermentation of a cell culture of tobacco;
   b) separation of the tobacco cells from the fermentation medium;
   c) homogenization of the tobacco cells in the presence of a detergent;
   d) boiling of the tobacco cells obtained in step (c) to remove pectins and starches and obtain cell walls;
   e) treatment of the cell walls obtained in step (d) with an acid solution to detach the sugars bound to proteins of the cell walls; and
   f) digestion of proteins of the cell walls by enzymatic hydrolysis with pepsin.

2. Method according to claim 1, characterized in that, it comprises between steps c) and d), a step of precipitating the cell walls and washing to remove cellular cytoplasmatic components.

3. Method according to claim 1, characterized in that the digestion of the proteins of the walls of step f) is carried out by alternating acid hydrolysis and enzymatic hydrolysis.

4. Method according to claim 1, characterized in that said cell culture is a culture of BY2 tobacco cells.

5. A composition obtained according to the method of claim 1.

6. A composition according to claim 5, characterized in that it comprises one or more polysaccharide units.

7. A composition according to claim 6, characterized in that said polysaccharide unit is arabinose or a fraction thereof.

8. A method for giving crops tolerance to abiotic and/or biotic stress which comprises applying to said crops a composition according to claim 5.

* * * * *